(12) United States Patent
Loong

(10) Patent No.: US 6,494,103 B1
(45) Date of Patent: Dec. 17, 2002

(54) LOAD CREATION APPARATUS AND METHOD

(76) Inventor: Chong Choon Loong, Block 121, Tampines Street 11 #04-286, Singapore (SG), 520121

(*) Notice: Subject to any disclaimer, the term of this patent is extended or adjusted under 35 U.S.C. 154(b) by 0 days.

(21) Appl. No.: 09/555,198

(22) PCT Filed: Nov. 25, 1998

(86) PCT No.: PCT/SG98/00095

§ 371 (c)(1),
(2), (4) Date: Jul. 19, 2000

(87) PCT Pub. No.: WO99/27330

PCT Pub. Date: Jun. 3, 1999

(30) Foreign Application Priority Data

Nov. 25, 1997 (SG) .............................. 9714136

(51) Int. Cl.[7] .......................... G01N 3/00; G01N 11/00
(52) U.S. Cl. ....................................................... 73/788
(58) Field of Search .......................... 73/788, 820, 836

(56) References Cited

U.S. PATENT DOCUMENTS 5,357,801 A * 10/1994 Sinclair ....................... 73/290

FOREIGN PATENT DOCUMENTS

| FR | 2554230 | 5/1985 |
|---|---|---|
| GB | 1457457 | 12/1976 |
| GB | 2047414 A | 11/1980 |
| GB | 2072351 A | 9/1981 |
| GB | 0887630 A1 | 12/1998 |

* cited by examiner

Primary Examiner—Benjamin R. Fuller
Assistant Examiner—Andre Allen
(74) Attorney, Agent, or Firm—Welsh & Katz, Ltd.

(57) ABSTRACT

A load creation apparatus is adapted to create a specified mass intended to be suspended such that a load bearing structure is able to bear the mass. The apparatus includes a liquid impervious container. The container is suspended from he load bearing apparatus by suspension means. The container is able to be filled with liquid to create the test mass. The mass of the container is obtained by means for determining the mass of liquid in the container from the density and volume of the liquid. A method is also provided for testing the ability of a load bearing structure to bear a specified test mass, created by such a load creation apparatus.

29 Claims, 12 Drawing Sheets

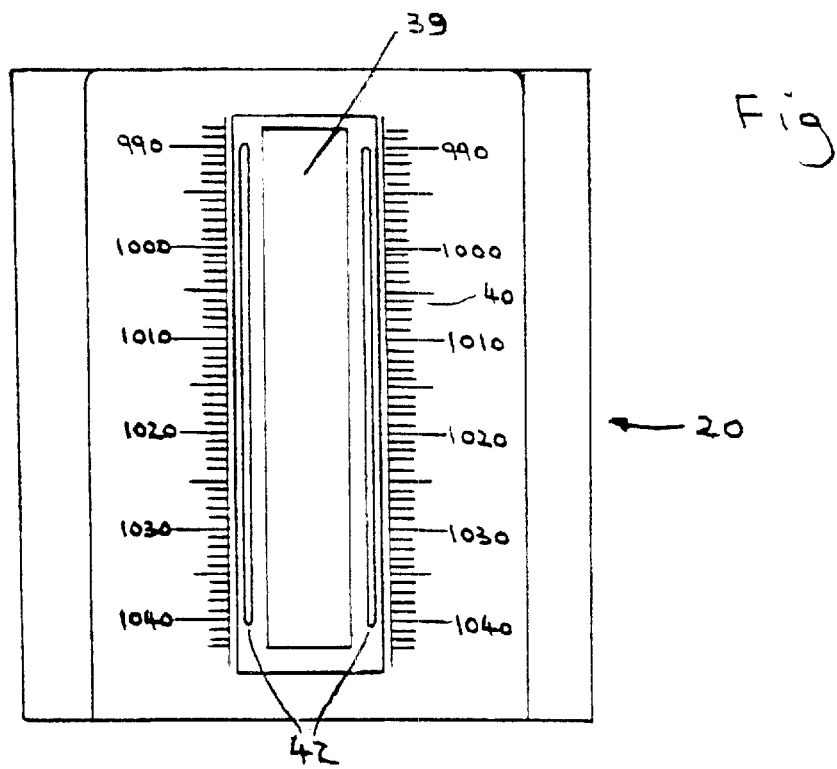
Fig 8
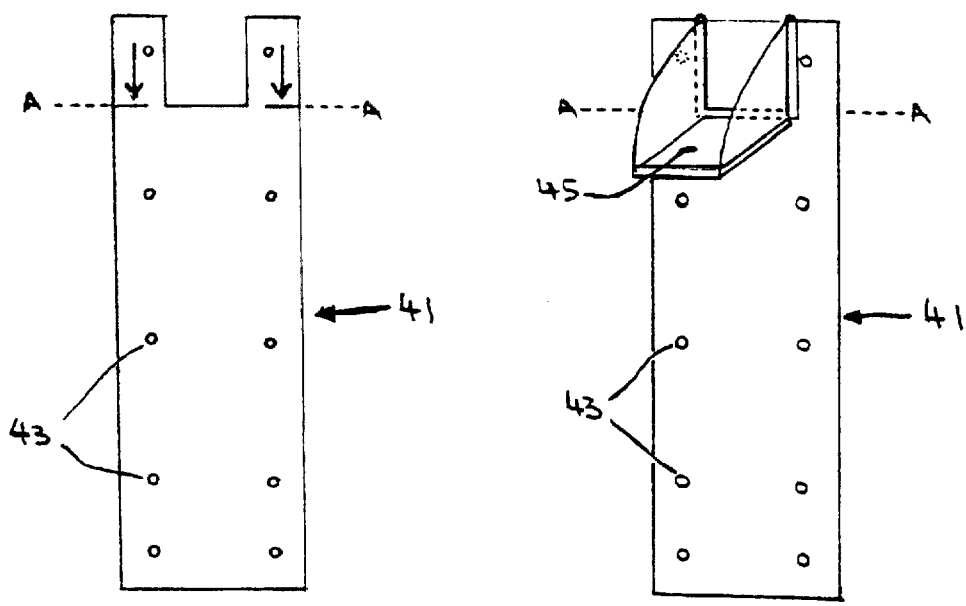
Fig 9
Fig 10

LOAD CREATION APPARATUS AND METHOD

FIELD OF INVENTION

This invention relates to load creation apparatus, and to a method of testing the ability of a load bearing structure to bear a test mass that is created using such a load creation apparatus. The invention relates particularly, but not exclusively, to loads which are used for testing the load bearing characteristics of hoists, cranes, davits, winches and other load bearing structures. The invention also relates to the testing of static load bearing structures, such as foundation piles, bridges, floors, jetties and wharves.

Specifically, the invention does not relate or extend to containers and apparatus in general that are not adapted or designed for load creation and testing purposes.

BACKGROUND

The ability of a load bearing structure to bear maximum loads will decrease with its length of service, due to wear and tear of the apparatus. For this reason, it is necessary and sometimes mandatory that load bearing apparatus, such as hoists, cranes, davits and winches be tested periodically to verify that the apparatus are still capable of functioning at the maximum load capacity. In addition, such tests may be required when substantial alteration or repairs are made to the apparatus.

The tests require the load bearing structure or apparatus to successfully bear a specified test load or, more precisely, a test mass. Typically, test masses are in the range of a few metric tonnes to more than a few thousand metric tonnes and, in most cases, are in the range of 25% in excess of the safe working load of the load bearing structure or apparatus. Earlier test masses have been made of concrete or metal. Over a period of time, such test masses made of concrete can chip or crack and may thus loose their original precision of mass due to wear and tear. Metal objects will tend to rust, and may in some cases suffer from metal fatigue or crack propagation. Furthermore, these tests are conducted only periodically. It is appreciated that between tests, the storage of these solid test masses can create an inconvenient storage problem. Furthermore, the problem is exacerbated when a range of test masses, required for different apparatus, must be stored.

In response to the problems inherent in the use of solid test masses, the use of flexible liquid-filled bags as test masses has been proposed in United Kingdom Patent No. 2,047,414B (Tonnes Force Testing Services Limited) and United Kingdom Patent No. 2,072,351 (Water Weights Limited). The bags used in these British patents consist of flexible envelopes that are filled typically with water in order to create the necessary test mass. The liquid-filled bags resemble generally pear-shaped objects that are supported either singly or in combinations to create the specified test mass. Since these flexible bags are collapsible when empty, they solve the problem of storage that is inherent in the use of metal or concrete test masses. However, while one set of problems is overcome, the use of water or liquid weights introduces a different set of problems that is inherent in the use of temporary masses, namely the problem of ensuring that the bag is filled with the correct amount of liquid to create a mass of the correct value.

This problem of filling the bag accurately with the correct amount of liquid must be seen in the light of the fact that the standards of weight testing often require the masses to be within relatively fine tolerances. For example, reference is made to British Standard BS 7121 Part 2: 1991 which is entitled "Code of practice for safe use of cranes. Part 2. Inspection, testing and examination". According to British Standard BS 7121, the test mass should be of proven accuracy to within ±1.0%.

Another factor that presents difficulties in creating a temporary mass within the acceptable margins is that the density of a liquid varies with composition and temperature. Consequently, changes in the liquid density affect the mass. A cubic meter of pure water at 40° C. weighs around 7.7 kg less than another cubic meter of water at 3.98° C. The density of pure water at 40° C. is around 992.3 kg m$^{-3}$, whereas at 3.98° C. it is around 1000 kg m$^{-3}$. The density of sea water taken from the open sea may vary between approproximately 1020 and 1030 kg m$^{-3}$. When expressed as the amount of salt per kilogram of sea-water, in terms of parts per thousand by weight (o/oo), the salinity of sea-water varies typically from 34 to 37 o/oo and has been found to be as low as 5 o/oo in the Finland and as much as 41 o/oo in the northern part of the Red Sea. The difference of density in sea water is caused mainly by the variation in temperature and salinity. Fresh water and sea water are the most common liquids used to fill the weight testing bags. Hence, if a bag is filled consistently with the same amount of liquid, the vagaries of liquid density means that the bag may not necessarily contain the same mass on each occasion. These variables mean that the amount of liquid required to fill the bag is not constant, and must be ascertained in the context of the ambient conditions. These factors explain why the task of filling bags, with what can amount to thousands of liters of liquid, is not simple task, especially when the amount of liquid may have to be within ±1.0% of a specified amount as required by certain mandatory standards.

The vagaries discussed above mean that it is often necessary to weigh the mass using a weighing device such as a load cell or dynamometer. Although weighing the mass, at the time of using the test mass, can ensure that the vagaries of the amount of liquid and the prevailing density of the liquid are taken into account, the use of a weighing device, in turn, presents another set of problems. It is appreciated that the calibration (and indeed the maintenance of that calibration) of weighing devices used for masses in the range of a few thousand tonnes is expansive and not straightforward. Furthermore, the precision of the calibration is lost progressively over time, which means that the expensive process of calibration must be repeated regularly. For example, in British Standard BS 7121, the weighing device or weighbridge used to ascertain the value of the mass must, at the time of conducting the test, have been calibrated and certified within the last twelve months.

In the field of weight testing, the weighing devices usually include electrical components and circuitry. The use of such electrical weighing devices presents peculiar problems in applications where inflammable materials are in close proximity. For example, when testing cranes that are used in petroleum production facilities, it is necessary to ensure that the electrical weighing devices are shielded, so that any sparks from the weighing device will not initiate ignition of the petroleum products in the vicinity.

Another type of load bearing structure which must be tested with a test load is found in the piles used as a foundation of buildings. A test method is defined in A.S.T.M. D 1143-8 (American Society for Testing and Materials) which is entitled "Standard Test Method for Piles Under Static Axial Compressive Load." After the foundation piles have been driven into the ground, the piles must be subjected to a static compressive load to test whether each pile has adequate load bearing capacity. The test loads are usually created by soil, rock, concrete, steel or water-filled tanks. These solid masses are usually solid, and are often in the form of large concrete blocks. Therefore, problems similar to the ones mentioned above in connection with solid test masses are experienced in transporting and positioning the large, solid masses on the test rig, and in storing the solid test masses when not in use. Furthermore, a weighing device in the form of a hydraulic jack is required to determine the actual test load, and this hydraulic jack must be regularly calibrated and certified. Other types of load bearing structures that must be tested with compressive loads include bridges, floors, jetties and wharves.

An object of the present invention is to overcome or substantially ameliorate at least some of the disadvantages of the prior art, and it is not intended that the invention in its broadest aspect must necessarily overcome all of the above-mentioned problems in the prior art.

SUMMARY OF INVENTION

According to the present invention, there is provided a load creation apparatus operatively adapted to create a specified mass which is suitably large for load testing a load bearing structure, comprising:

a liquid impervious container;

means for filling the container with liquid to create the specified mass therein;

suspension means for suspending the container such that said load bearing structure is able to bear said specified mass; and wherein the container is provided with determination means for determining the mass of the liquid which forms the specified mass in the container, the mass being determined from the density and volume of the liquid.

The determination means may be provided in the form of said container being substantially shaped as a regular geometric shape at least at those regions that are adjacent the liquid in the container such that the volume of liquid in said container is readily calculable.

The determination means may be provided in the form of said container being provided with walls which, in use, are upright at least at those regions that are adjacent the liquid in the container.

Preferably, the walls, in use, are generally vertical at least at those regions that are adjacent any liquid in the container.

The determination means may be provided in the form of said container being provided with a base that has a predetermined surface area.

The base may be orthogonal, and the base may be level.

The determination means may include a calibrated gauge which provides a visual indication of the level of liquid to which the container must be filled when the liquid has a particular density.

The visual indication may be adjustable in accordance with the density of the liquid.

The liquid impervious container may be made of flexible material.

The means for filling may be in the form of an opening for said container.

The means for emptying the container may be in the form of liquid discharge valve in the base of the container.

The suspension means may be in the form of a central strap which extends generally through the center of gravity of said container when liquid is in the container.

The container may be divided into partitions by an internal web that connects internal surfaces of the container, said web functioning as a structural brace for the container when the container contains liquid.

Liquid may be able to flow from one partition to an adjoining partition through vents located in the web.

Alternatively, the walls of the container may be provided with flat reinforcing components which enable the walls, in use, to remain upright.

Alternatively, or in addition to the reinforcing components, at least some of the walls of the container may be connected one to another with reinforcing struts, each of the struts functioning as a structural brace for the container when the container contains liquid.

According to another aspect of the invention, there is provided an arrangement for creating a specified mass for testing a load bearing structure comprising a plurality of load creation apparatus each of which are suspended, wherein said plurality of apparatus are juxtaposed with respect to one another.

The juxtaposed apparatus may be connectable by vents that enable at least one of the apparatus in the arrangement to be filled with liquid received from at least one other of said plurality of apparatus.

The vents may be in the form of a flexible duct that is able to interconnect adjacent apparatus.

The apparatus may be used for testing the ability of a load bearing structure to bear a specified test mass.

The arrangement may be used for testing the ability of a load bearing structure to bear a specified test mass.

According to a further aspect of the invention, there is provided a method of testing the ability of a load bearing structure to bear a suitably large specified test mass, comprising the steps of:

using suspension means to suspend at least one load creation apparatus such that the load bearing structure is able to bear a specified mass created by said load creation apparatus, said apparatus comprising a liquid impervious container;

filling said container with liquid to create said specified mass therein; and using determination means provided on said container to determine said mass of the liquid which forms the specified mass in the container, the mass being determined from the volume and density of the liquid.

The method may involve the step of ascertaining the volume and density of the liquid and thereby determining the mass of the liquid therefrom.

Preferably, the determination means are provided in the form of said container being provided with walls which, in use, are upright at least at those regions that are adjacent the liquid in the container and said container being provided with a base that has a predetermined surface area, and wherein said method involves the step of calculating the volume of said liquid by multiplying the base surface area by the height of said liquid in the container and determining the value of the mass of the liquid therefrom.

The method may involve the step of ascertaining the density of liquid and thereby determining the amount of liquid with which to fill the container in order to produce the specified mass.

A plurality of said apparatus may be suspended in accordance with the abovementioned arrangement.

Liquid may be poured initially into one of said plurality of apparatus, and liquid from said one apparatus may flow to at least one other of said plurality of apparatus.

Preferably, one of more of said other apparatus are provided each with a valve which prevents the liquid from escaping from the apparatus such that the liquid is constrained to flow to at least one other of said apparatus until all the apparatus in the arrangement have been substantially filled to the required level.

The valve may be a float valve that is opened and closed by a floatable mechanism.

According to yet a further aspect of the invention, there is provided a load creation apparatus operatively adapted to create a specified mass which is suitably large for load testing a load bearing structure, comprising:

a liquid impervious container;

means for filling the container with liquid to create said specified mass therein; and suspension means for suspending the container such that said load bearing structure is able to bear said specified mass;

wherein said container is provided with upright walls which are arranged and operatively adapted to determine the volume of the liquid therein, so that the specified mass created by the liquid in the container is able to be determined by reference to the density of the liquid.

The apparatus may be used for testing the ability of a foundation pile to bear a specified test mass.

The arrangement may be used for testing the ability of a foundation pile to bear a specified test mass.

The load bearing structure may be a hoist, crane, davit, winch or other similar load bearing structure.

In the specification and claims, it is said that the test mass is intended to be suspended such that a "load bearing structure" is able to bear the test mass. The word "structure" is not intended to introduce any limitation on the type of structure, apparatus or machine that is able to be tested. For example, embodiments of the invention may be used for testing lifting machines such as hoists, cranes, davits and winches where the load is suspended from the apparatus. Other embodiments of the invention may be used to create a compressive load to be borne by load bearing structures such as structural foundation piles. The invention may be used to test a wide range of load bearing device which must be tested with a specified test mass.

In the specification, the word "filled" is used in the descriptive sense of adding liquid to the container. The word "filled" is not intended to imply that the container must necessarily be filled to the brim.

DRAWINGS

In order that the invention might be more fully understood, embodiments of the invention will be described, by way of example only, with reference to the accompanying drawings, in which:

FIG. 8 shows an embodiment of a calibrated density gauge positioned adjacent a slit;

FIG. 9 shows a plate that is usable with the density gauge of FIG. 8;

FIG. 10 illustrates a modification of the plate of FIG. 9, a difference being that the plate in FIG. 10 is provided with a pivoting float valve that guards the opening at the upper end of the plate;

Figure 1:
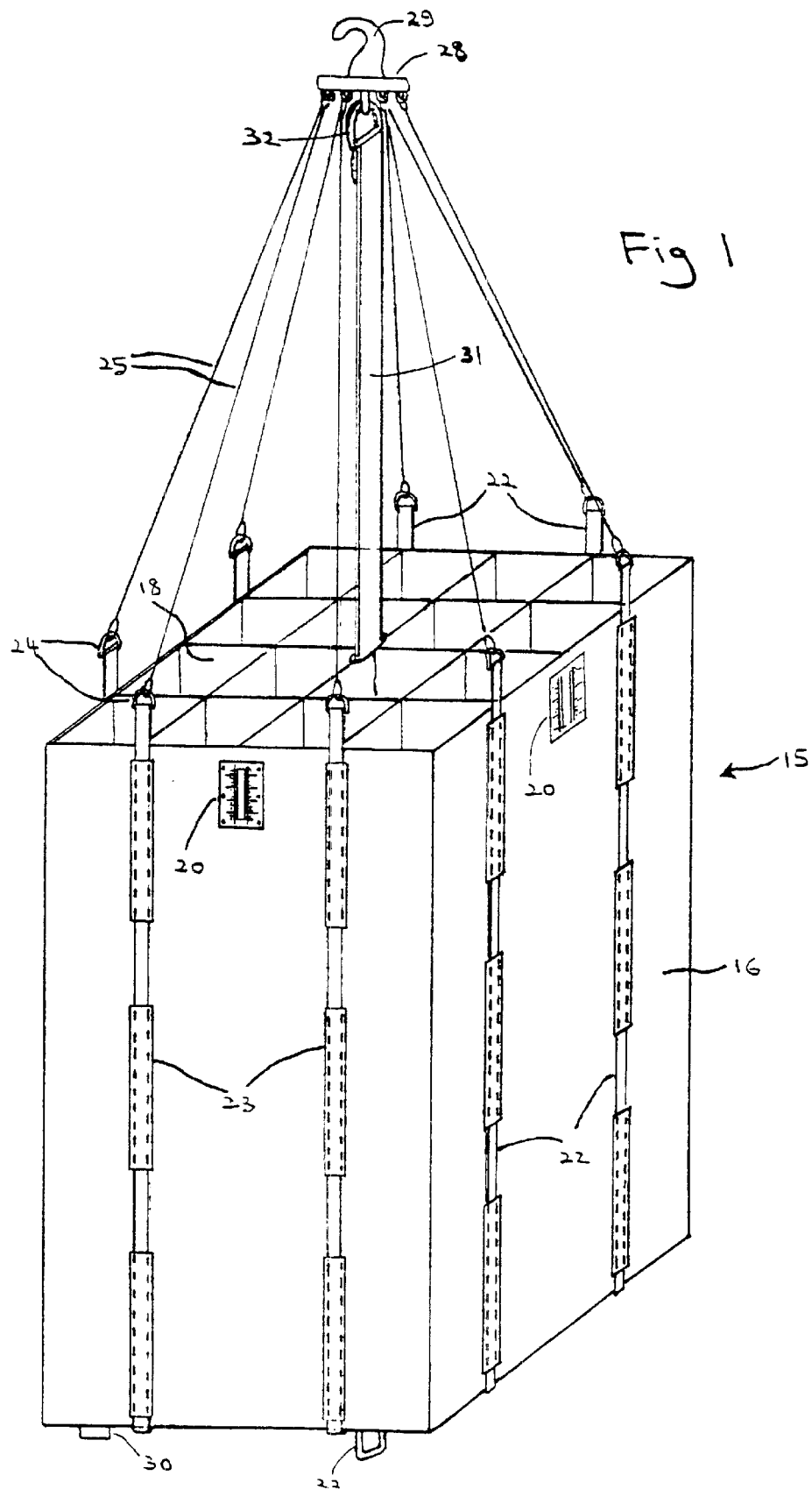
FIG. 1 shows a perspective view of an embodiment of a load creation apparatus.

In the embodiment and drawings, similar components are numbered with the same numerals for the sake of simplifying the understanding of the description. For example, the containers are labeled in the each of the Figures with the same reference numeral "16", and the plate in FIG. 9 is given the same number of "41" as in FIG. 10 although the two plates relate to different modifications. Hence, the similarity in numbers should not be taken to imply that the features in each embodiment need necessarily be of identical design.

EMBODIMENTS

Figure 2:
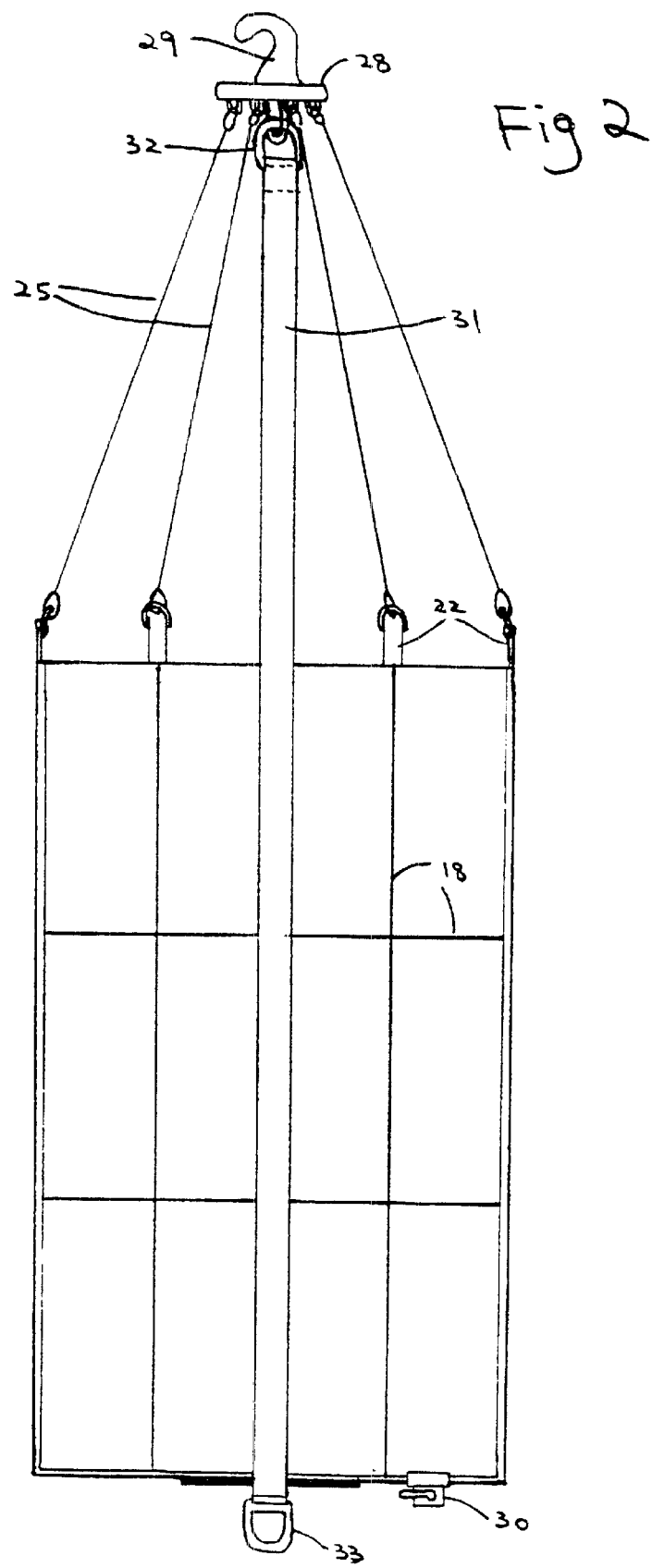
FIG. 2 shows a cross-sectional view of the embodiment of the load creation apparatus in FIG. 1.
Figure 3:
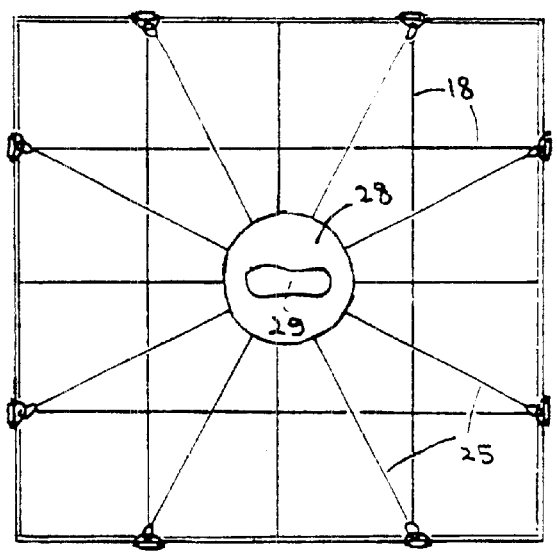
FIG. 3 is a plan view of the embodiment of FIGS. 1 and 2.

Referring to the drawings, FIG. 1 shows a perspective view of an embodiment of a load creation apparatus, which is generally indicated as 15. The embodiment is shown in FIG. 2 from a side view, and in FIGS. 3 and 4 from a plan and under-side view respectively.

The load creation apparatus 15 is provided with a liquid impervious container in the form of container 16. The container 16 is made of a woven polyester fiber coated with PVC that is blended with a special resin, but may also be made from any suitable tough, liquid impervious material.

The liquid impervious container 16 is provided with means for filling the container with liquid. In the present embodiment, this is provided simply as an open top for the container through which liquid is able to be poured. Other alternatives may have the container provided with a closed top with a restricted liquid inlet.

The liquid impervious container 16 is also provided with means for emptying the container which, in the embodiment, is in the form of liquid discharge valve 30 located in the base of the container.

It is anticipated that fresh water and sea water will be the usual type of liquids used to fill the apparatus and arrangements described and defined herein, because these liquids are readily available from natural sources and are cheap. However, other liquids may be used at the discretion of the user.

When the container 16 is filled with a sufficient mass of liquid, the resulting mass is suitable for use as a test load that can be suspended, such that a load bearing structure under test (not shown) is able to bear the mass in the container 16. The load bearing structure or devices may be a hoist, crane, davit, winch, or other pulling or lifting machine or any such device that must be tested by suspending a specified load. These may also include static load bearing structures such as foundation piles.

Figure 4:
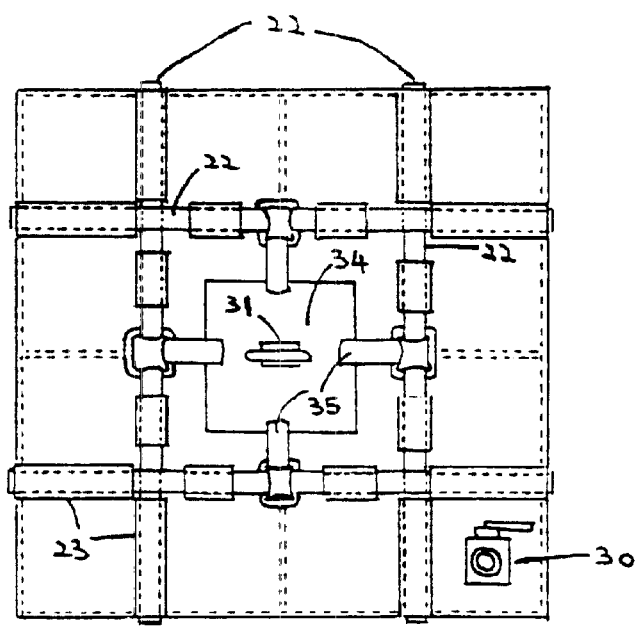
FIG. 4 is an under-side view of the embodiment of FIGS. 1, 2 and 3.
Figure 6:
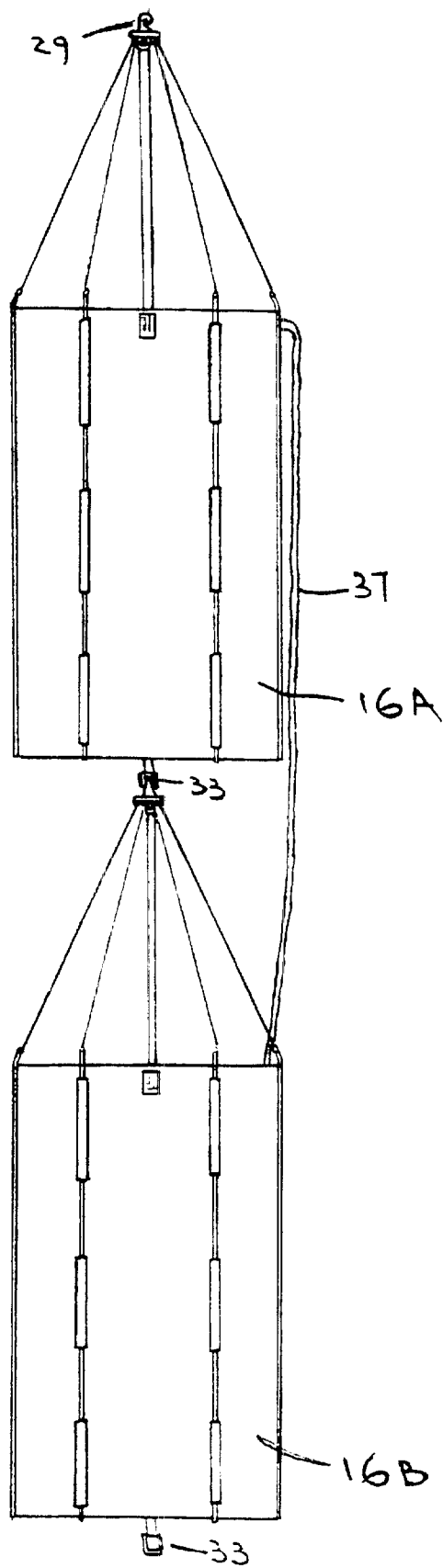
FIG. 6 illustrates a further embodiment of the invention consisting of an arrangement of two load creation apparatus positioned one above the other.

The apparatus 15 is also provided with suspension means for suspending the container 16 such that a load bearing structure (not shown) is able to bear the mass in the container. The suspension means, in the embodiment, includes a central strap 31 which extends generally through the center of gravity of the container 16 when it contains liquid. In FIG. 2, the strap passes through a sleeve running through the center of the container 16. The bottom end of the strap is provided with an oversized eyelet 33 that prevents the central strap 31 from pulling through the sleeve. The eyelet 33 serves a further function of enabling another container to be suspended beneath the present container 16. (Such an arrangement is illustrated in FIG. 6.) Referring to FIG. 4, a reinforced PVC plate 34 is provided at the base of the container to act as a further reinforcement for the central strap 31, in order to anchor the end of the strap to the base of the container. In FIG. 2, the top end of the strap is provided with an attachment means in the form of a hook 29. The hook is formed with a supporting boss 28. The underside of the boss 28 is provided with an eyelet. The hook 29 is detachably fastened to the central strap 31 by means of a shackle 32 that passes through the eyelet that is on the underside of the boss 28. The central strap 31 carries the bulk of the mass in the container 16. The support means for the container 16 may also include secondary supports 25 that extend from the hook 29 to the peripheral edges of the container 16. Thus, the entire apparatus 15 is able to be suspended from the load bearing structure using the hook 29 to suspend the container, aided by the central strap 31 and the secondary supports 25, such that the load bearing structure is able to bear the mass of the apparatus 15.

In FIG. 1, the secondary supports 25 are attached to the container 16 by being connected to external straps 22 that are evenly spaced around the upper rim and sides of the container. The ends of the external straps 22 are provided with shackles 24 to facilitate attachment of the external straps 22 to the secondary supports 25. The external straps 22 extend down the side of the container and, as seen in FIG. 4, the external straps 22 surround the underside of the container and undergrid the container 16. The container is effectively cradled in a web of external straps 22. In FIGS. 1 and 4, the external straps 22 pass through sleeves 23 located on the side faces and on the under-surfaces of the container. The sleeves 23 hold the external straps 22 in place. On the under-surface of the container as seen in FIG. 4, additional strengthening straps 35 are used to connect the web of external straps 22 to the reinforced PVC plate 34. The reinforcing plate 34 is thus joined to both of the external straps 22 and the central strap 31. The plate 34 therefore acts as a connection between the central strap 31 and external straps 22. The internal and external straps are thus able to co-operate to support the mass in the container.

If, due to the size of container, there is found to be a tendency for the secondary supports a deform the defined shape of the container by pulling the edge margins of the container towards the central axis of the container, then in order to counter-act this tendency, the edge margins or rim of the container may be provided with some form of structural reinforcement. The reinforcement may be in the form of struts that brace the rim of the container in its intended shape. Furthermore, the face of the container may also be provided with reinforcing plates to enable the container to maintain its overall defined shape.

The central strap 31 and the secondary supports 25 are made of webbing material or other suitable weight-bearing material. For extremely heavy test loads, the strap and the secondary supports may be reinforced with or made entirely of wire, or other suitable strong material.

Determination Means

An important feature of the present invention is that the container of each load creation apparatus is provided with determination means for determining the mass of any liquid in the container from the density and volume of the liquid.

The invention relies on the fact that the mass of liquid is able to be determined from the volume and density of the liquid. The relevant equation is:

$$\text{Liquid Mass (kg)} = \text{Liquid Volume (m}^3\text{)} \times \text{Liquid Density (kg m}^{-3}\text{)}$$

The mass is a constant and is fixed by virtue of the size of the load specified in the load test. The figure would probably be specified by the manufacturer of the load bearing structure or by a certification authority. When the density of the liquid is measured, the above equation shows why the volume of liquid is inversely proportional to the liquid density. In other words, if the density and volume are known, then the mass of the liquid is able to be determined, without the need for a weighing device or apparatus. This is the basis of how the present embodiment is able to avoid the use of a weighing device for determining the mass of the liquid.

The user is able to ascertain the density of the liquid using a hydrometer. Common liquids, drawn from large reservoirs such as the sea or rivers, take a long time to change temperature in response to changes in ambient temperature. Once the liquid density has been measured, it is found that the density reading is generally constant for a period of time usually sufficient for the load test to be performed.

In the present embodiment, the user makes use of the determination means to ascertain the required level of liquid with which the container must be filled. However, other embodiments may use other forms of determination means that are designed to automatically control the required amount of liquid.

Calculating the Mass by Determining the Volume and Density

In the embodiment shown in FIGS. 1 to 4, the means for determining the mass of liquid in the container is present in the form of the container 16 being substantially shaped as a regular geometric shape, at least at those regions that are adjacent the liquid in the container such that the volume of liquid in the container is readily calculable. Hence, the embodiments of the invention can include containers shaped in any regular geometric shape, so long as it is possible to readily perform accurate calculations to ascertain the volume.

Upright Walls

However, in the most convenient embodiments, the container 16 is provided with walls which, in use, are upright at least at those regions that are adjacent the liquid in the container. When the container is made of flexible material, only those portions of the container that are filled with liquid would normally take on the final shape. Without liquid in the container, the upper portions of the container may sag slightly, but this is not critical provided that these portions do conform to the final defined shape when water is filled to up those levels.

The upright walls enable the volume of the liquid to be ascertained simply by multiplying the surface area of the base by the height of the liquid in the container. Accuracy is ensured when the walls are generally vertical at least at those regions that are adjacent any liquid in the container. Strict compliance with 90° uprightness, although desirable, is not strictly required, provided that the amount of divergence does not cause the mass of liquid to vary outside the prescribed limits. For example, in the British Standard BS 7121, the mass must be ±1.0%, and the degree of the measurement and arrangement of the walls of the container 16 must be such as to ensure that the necessary precision is attainable.

The calculation is more readily performed if the base has a known area, and if the base is kept generally level during use. The invention in its broadest aspect does not require the base to be orthogonal, since it is sufficient for the base surface area to simply be known so that it can be multiplied by the height. Hence, the shape of the base may be orthogonal, square, rectangular, circular or any other shape. However, it is preferred that when using more than one such container in an arrangement, having an orthogonal-shaped base means that it is easier to arrange the containers closely side by side. (This feature will be discussed below.) It is preferred, however, that the base is square because it retains the benefit of having an orthogonal shape, while also ensuring that the mass of liquid in the container will be evenly distributed about the centre of gravity, as compared to more elongated-shaped bases.

Hence, it is apparent that the use of upright walls in the present embodiment in FIGS. 1 to 4 is a feature that confers an advantage on the apparatus. The advantage of having upright walls is that the volume of the liquid may be calculated readily by simply multiplying the base area by the height of the liquid contained in the upright container. Further embodiments of the upright walls will be discussed in the context of arrangements consisting of a plurality of containers.

It is appreciated that in the amorphous pear-shaped bags found in the two abovementioned prior art United Kingdom patents, it would be difficult to calculate the height of liquid. The natural pear-shape of earlier weight test bags was considered acceptable and not modified because, in the prior art, the shape was not considered to be a factor that influenced the test procedure. In the prior art, where the mass is determined by a calibrated weighing device, the sole function of the bags was to contain the liquid. The shape of the bag was not considered to have a bearing on the test result. Hence, the bags in the prior art were made of flexible material and allowed to accommodate the liquid by finding their own natural shape without any restrictions on the defined shape of the bag.

In use of the present embodiment, the load creation apparatus 15 in FIG. 1 is suspended in such a manner that a load bearing structure (not shown), such as a crane for example, is able to bear the created load. The container 16 is the load creation apparatus 15 is filled with liquid. The density of the liquid is ascertained with a hydrometer, and then the volume of liquid (and hence the height of liquid) required to produce the mass specified for a test is ascertained. The container is filled with liquid up to the height required to produce the specified mass. Thus, the specified mass is achieved accurately, without the need of a weighing device. This type of apparatus and this method are thus free of the potential problems associated with weighing devices which tend to lose accuracy and/or precision over a period of time.

The walls or panels of the container 16 are made of flexible materials, but the container, when filled with liquid, is not flexible in the sense that the container does not permit the liquid to find its own shape. The shape of the container 16 is achieved intentionally by providing the container with flat sheet-like orthogonal walls. However, in practice, having merely four upright walls and a flat base is sufficient only for containing very small masses of liquid. For larger masses of liquid, the liquid would cause the walls of a simple open topped container to bulge outwards under the force of the liquid attempting to find its own shape. Since the shape of the container 16, in the present embodiment, is important to the working of the apparatus, the container 16 is divided into partitions by an internal web 18 that connects internal surfaces of the container. The web counter-acts the tendency of the walls to bulge outwards under the influence of the water pressure. The web therefore functions as a structural brace for the container when it contains liquid. As shown in FIG. 1, there may be one or more of such webs. The webs may intersect. Liquid is able to flow from one partition to an adjoining partition through vents located in the web. The webs provide sufficient bracing to enable the container to retain its shape adequately when the container is filled substantially with liquid. When creating extremely large masses, the flexible faces of the container 16 may be further reinforced with sheets of plates made of rigid material such as PVC.

Figure 4A:
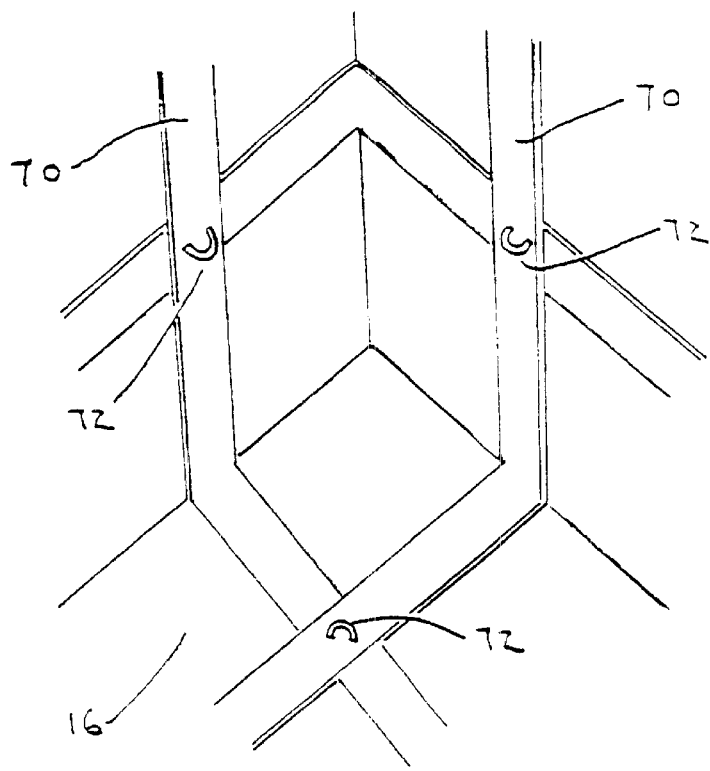
FIG. 4A is a perspective drawing of a further embodiment showing an internal corner of a container having reinforcing strips attached to the internal surfaces.

While the use of internal webs 18, mentioned above, provides adequate structural rigidity for the container, other embodiments may use alternate forms of structural reinforcements that may cost less to manufacture. Accordingly, instead of having the container divided into partitions through the use of reinforcing webs 18, a further embodiment shown in FIG. 4A uses flat reinforcing components which enable the walls, in use, to remain upright. The reinforcing components are in the form of reinforcing strips 70 which reinforce the faces of the container 16. The reinforcing strips 70 are attached or fastened to internal faces of the container, as shown in FIG. 4A. However, the reinforcing components may also be attached to external faces of the container. These reinforcing strips 70 contribute adequate structural reinforcement to the container 15. The strips are made of a suitably stiff material or webbing, such as those that contribute a high degree of stiffness, similar to those used in conveyor and pulley belts. The reinforcing strips may be flat, as illustrated in FIG. 4A, or the reinforcement may be in the form of stiff rods (not shown). The reinforcing components may also be in the form of flat stiff panels that are attached to the sides of the container. Other suitable materials are PVC, polyester or fibreglass. When the container is filled with liquid, the reinforcing strips 70 provide stiffness to the faces of the container which enables the container to maintain the lateral faces in an upright disposition.

Figure 4B:
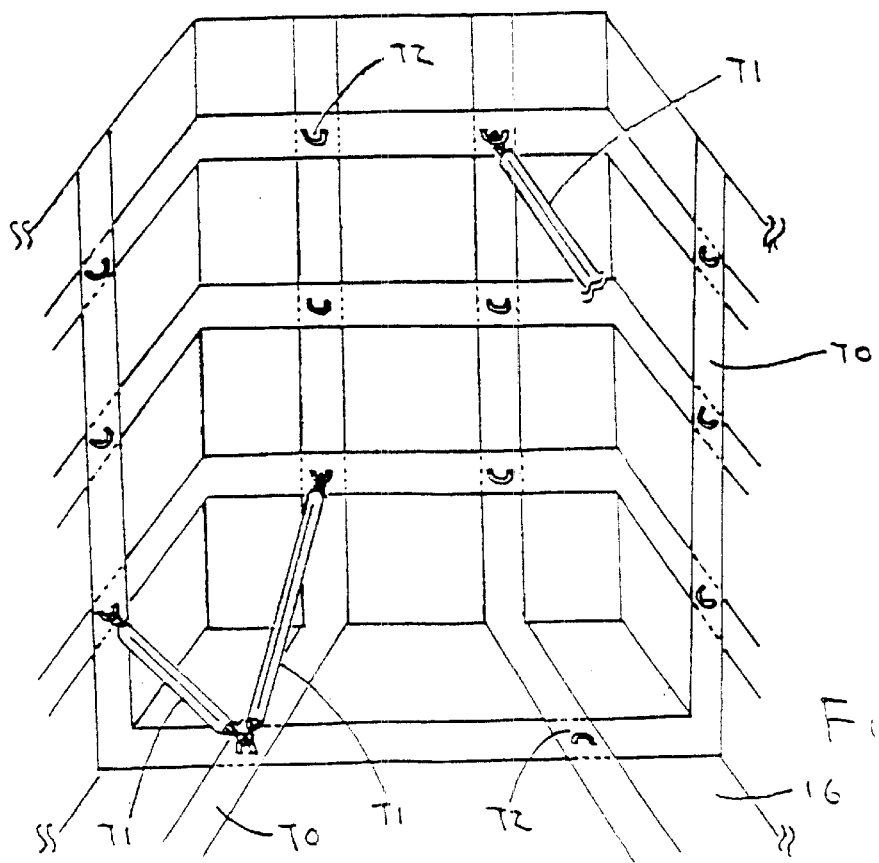
FIG. 4B shows a cross-sectional view of a modification of the embodiment in FIG. 4A in which the reinforcing strips are provided with reinforcing struts to reinforce the surfaces of the container.

In a further embodiment shown in FIG. 4B, as an alternative to, or in addition to the reinforcing strips 70, faces of the container are connected with reinforcing struts 71 that are used to brace the sides of the container by linking surfaces of the container one to another. The struts 71 are detachable. The reinforcing struts 71 can be made of solid or flexible material. Flexible struts are acceptable since these are able to provide structural reinforcement when the strut is in tension. The struts 71 may be in the form of strips or may be in the form of solid components. The surfaces of the container are provided with shackles 72 that are used to connect the reinforcing struts 71 to the inner surfaces of the container. It is possible for these struts 71 to act as an alternative to using the reinforcing internal webs 18. When the container is filled with water, the struts 71 are placed in tension to hold the lateral faces of the container in the necessary upright disposition.

Calculating the Mass by Determining the Density Alone

The "means for determining the mass of the liquid" of the load test apparatus of FIG. 1 is provided with a further enhancement which is based on the following equations used for calculating mass:

$$\text{Liquid Mass (kg)} = \text{Liquid Volume (m}^3\text{)} \times \text{Liquid Density (kg m}^{-3}\text{)}$$

$$\text{Liquid mass (kg)} = \text{Container base area (m}^2\text{)} \times \text{Liquid height (m)} \times \text{Liquid density (kg m}^{-3}\text{)}$$

When the above equations is applied to the context of the present embodiment, the following are constant: liquid mass, liquid density and container base area. (The mass is specified by the test to be conducted. The density is ascertained from ambient conditions, and the base area is a fixed value.) Consequently, the only variable in the equation is the height of the liquid in the container. The height of liquid is inversely proportional to the density of the liquid.

Based on this principle, the load creation apparatus 15 is provided with a calibrated gauge shown in FIG. 8. The calibrated gauge is in the form of a liquid density meter 20. The density meter 20 provides a visual indication of the level of liquid to which the container must be filled, when the liquid is at a particular density. The meter 20 is adjustable to take into account variations in the density of the liquid arising from changes in ambient conditions.

In the embodiment of FIG. 1, calibrated gauges are provided on all four sides of the container 16. Essentially, each meter 20 provides a scale, in this case, ranging from liquid densities of 0.990 g/cm³ to 1.040 g/cm³, which is a typical range of densities of fresh water and sea water. The scale provides an indication of the height of liquid to which the container 16 must be filled in order to achieve a specified mass. For example, a container designed to create a ten tonne mass would have a liquid density meter 20 that would indicate the correct amount of liquid necessary to achieve a mass of ten tonnes. This meter would be adjustable so that the user would know how much the vary the height of the liquid, depending on the prevailing liquid density, in order to achieve a mass of ten tonnes. The above equation teaches that the lower the density of the liquid, the larger amount of liquid that required to be poured into the container 16, and vice versa.

In a simple embodiment, the calibrated gauge is simply a scale that has been positioned accurately on the container, so that for each density value, the scale indicates the height of liquid, corresponding to that density, that is required to achieve the specified mass.

Figure 9A:
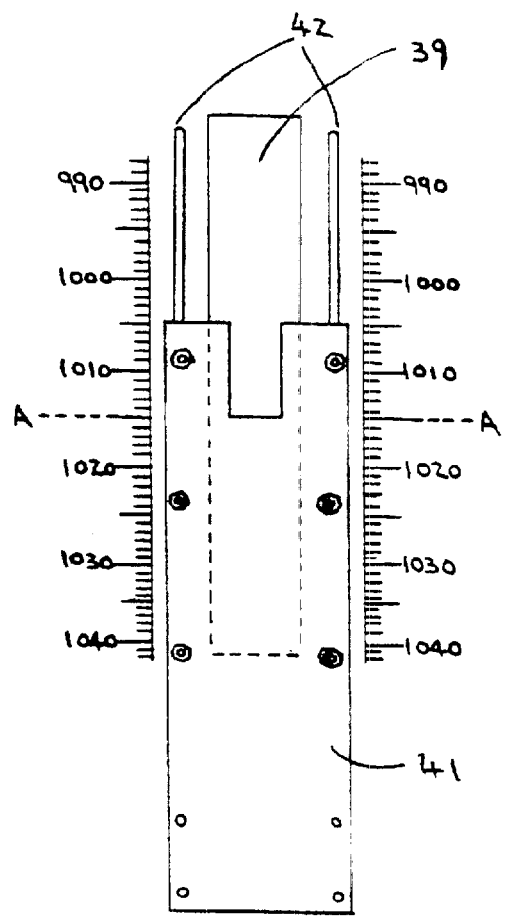
FIG. 9A shows the plate of FIG. 9 slideably and fastenably mounted in the slot shown in FIG. 8.

A further embodiment of a calibrated gauge is shown in FIGS. 8 and 9. In this embodiment, a calibrated density scale 40, ranging from liquid densities of 0.990 g/cm³ to 1.040 g/cm³, is located on the side margin of an elongated slit 39. Liquid in the container is able to exit the container through the slit 39. A pair of grooves 42 is provided on either side of the slit 39. The grooves together form a slot on which a plate 41 is slidably mounted, as seen in FIG. 9A. The edge margins of the plate 41 are provided with a resilient coating, perhaps in the form of a rubber, polymer foam or any such resilient material that can enhance the liquid-tight seal that is preferably formed between the plate 41 and the grooves 42. The plate 41 functions in a similar manner to a sluice valve that is slideable up and down in the slot. Thus, the liquid in the container 16 is only able to exit through the slit 39 after the liquid reaches the level of the top end of the plate 41, marked A—A in the drawing. Thus, the level of liquid in the container 16 is controllable by sliding the plate 41 up and down between the grooves 42. The positioning of the plate in the grooves is determined by the density scale 40. In FIG. 9A, the plate is positioned to set the required height of the liquid has a density of 1.015 g/cm³. The plate is able to set the upper height of the liquid in the container, because an excess liquid will flow out of the container once the liquid reaches the height A—A of the plate. Hence, the gauge in FIGS. 8, 9 and 9A acts as a sluice valve which is able to vary the level of liquid in the container 16. In FIG. 9A, once the liquid reaches the level set by the upper end A—A of the plate, any excess liquid flows over the end of the plate and out of the container 16 through the slit 39. The plate is provided with holes 43 which are used in conjunction with some form of fastening device such as screws to fix the plate to the slot in the required position.

Since the testing of the load bearing structure is concerned essentially with testing whether the structure is able to bear a specified mass, it is appreciated that the weight of the container itself 16 and the weight of the shackles, web, straps etc., will also add to the total mass that is borne by the structure. Therefore, when designing the calibrated gauge, it is preferred that the weight of the components be considered as part of the overall equation, as follows:

$$\text{Test mass (kg)} = \text{Liquid volume (m}^3\text{)} \times \text{Liquid density (kg m}^{-3}\text{)} + \text{Apparatus mass (kg)}$$

In further embodiments, an apparatus such as in FIG. 1 may be used to create a range of masses. To facilitate this, the calibrated gauge may be designed to indicate the heights of liquids required for a range of masses. Alternatively, a set of different gauges may be provided for the user to select the appropriate gauge, depending on the mass to be created. Charts may also be provided for making such modifications of mass.

Arrangement of Plurality of Containers

For very heavy test masses, two or more load creation apparatus are able to be suspended and juxtaposed with respect to one another.

Figure 5:
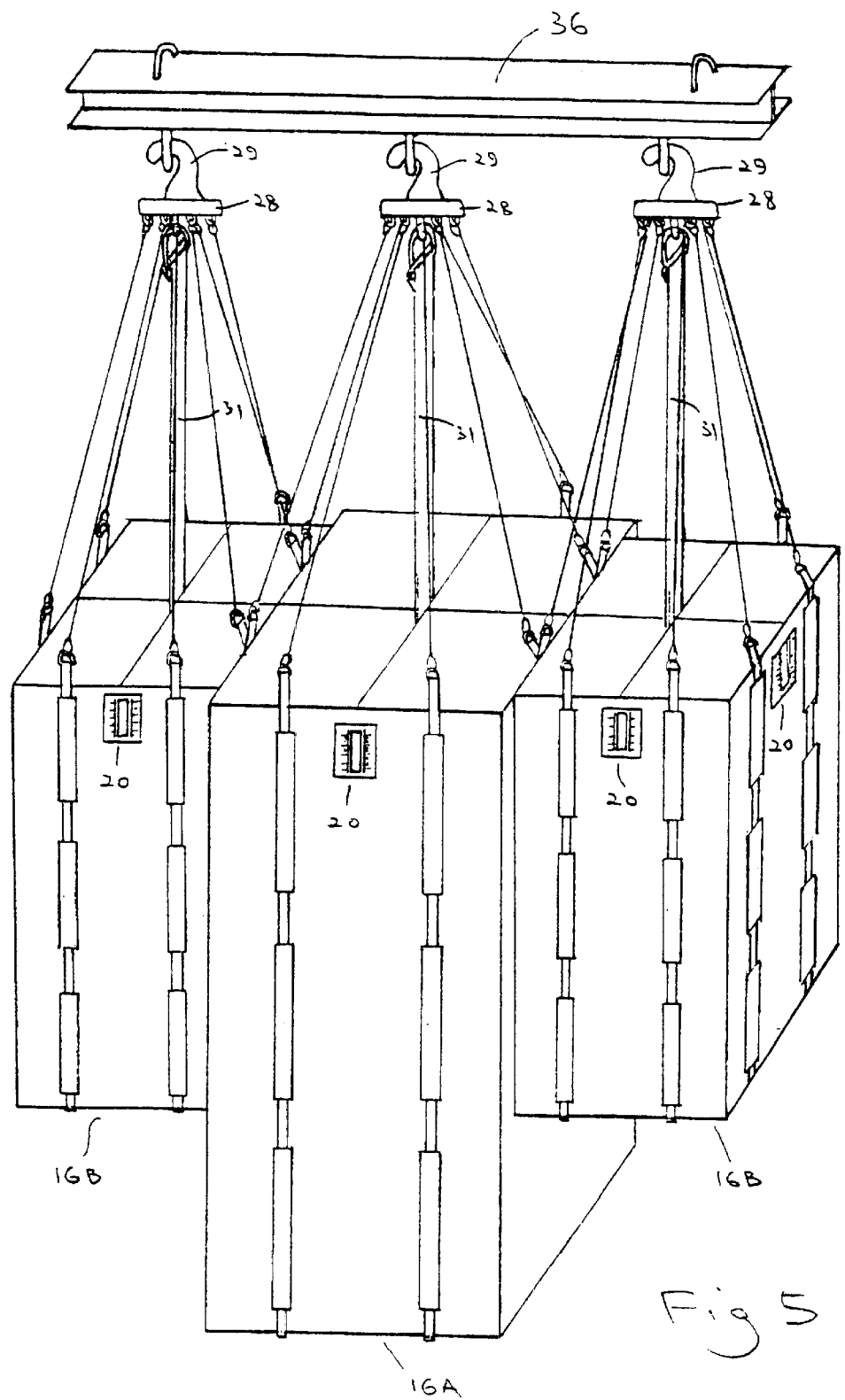
FIG. 5 illustrates another embodiment of the invention consisting of an arrangement of three load creation apparatus.

Containers are available in a variety of standard weights, each intended to create a particular mass. A plurality of these containers can be combined to form the total mass required. When creating an arrangement of two or more containers, the overall stability of the arrangement must be considered. For example, in order to create a nine tonne load, an arrangement of a five tonne container, sandwiched between a pair of two tonne containers, would provide better stability than, say, an arrangement of a five and four tonne container. For example, FIG. 5 illustrates an arrangement of three load creation apparatus that are suspended from a beam 36. (The beam is suspended from a load bearing apparatus). The apparatus are juxtaposed with respect to one another. The containers 16B, on either side of the central container 16A, are of equal capacity to ensure the stability of the overall arrangement.

As mentioned above, the upright walls of the container provide an advantage of being able to readily determine the volume of liquid in the container. In an arrangement consisting of a plurality of apparatus, the upright walls provide a further advantage in that the surfaces of each container are able to juxtaposed closely to an adjacent container. This is in contrast to the prior art. When the pear-shaped amorphous bags, disclosed earlier in the United Kingdom patents 2,047, 414B and 2,072,351 are used in arrangements of more than one bag, the pear-shaped bags cannot be juxtaposed as closely to one another as those containers of embodiments of the present invention that have upright walls. Thus, the arrangements of the type shown in FIG. 5 tend to take up less space than arrangements that use the earlier pear-shaped amorphous bags. Similarly, it is appreciated that the apparatus are able to be more closely juxtaposed when the base of the container of the apparatus are orthogonally-shaped, such as in the shape of a square or rectangle.

Figure 11:
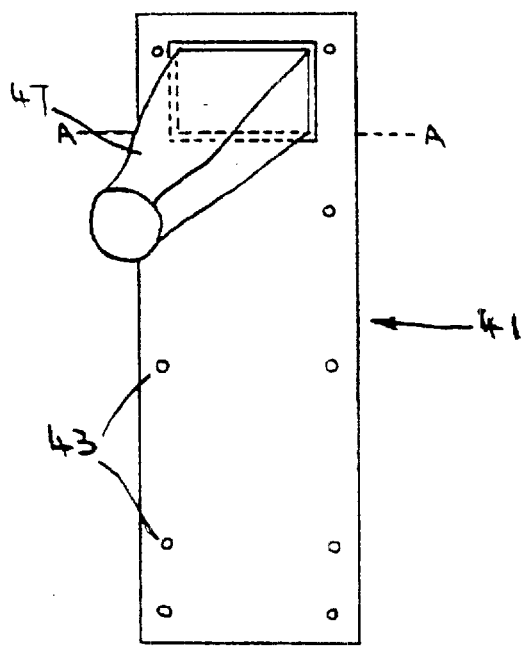
FIG. 11 illustrates an embodiment of a vent that is usable for connecting one load creation apparatus to another.

In arrangements that use a plurality of load creation apparatus, it is a preferred, but not essential, that the juxtaposed containers are connectable by vents that enable at least one of the containers in the arrangement to be filled with liquid received from at least one of the other containers in the arrangement. Liquid flows from container to container through the vents. The vents are in the form of flexible ducts 47 that interconnect adjacent containers. An example of a vent is shown in FIG. 11.

Figure 12:
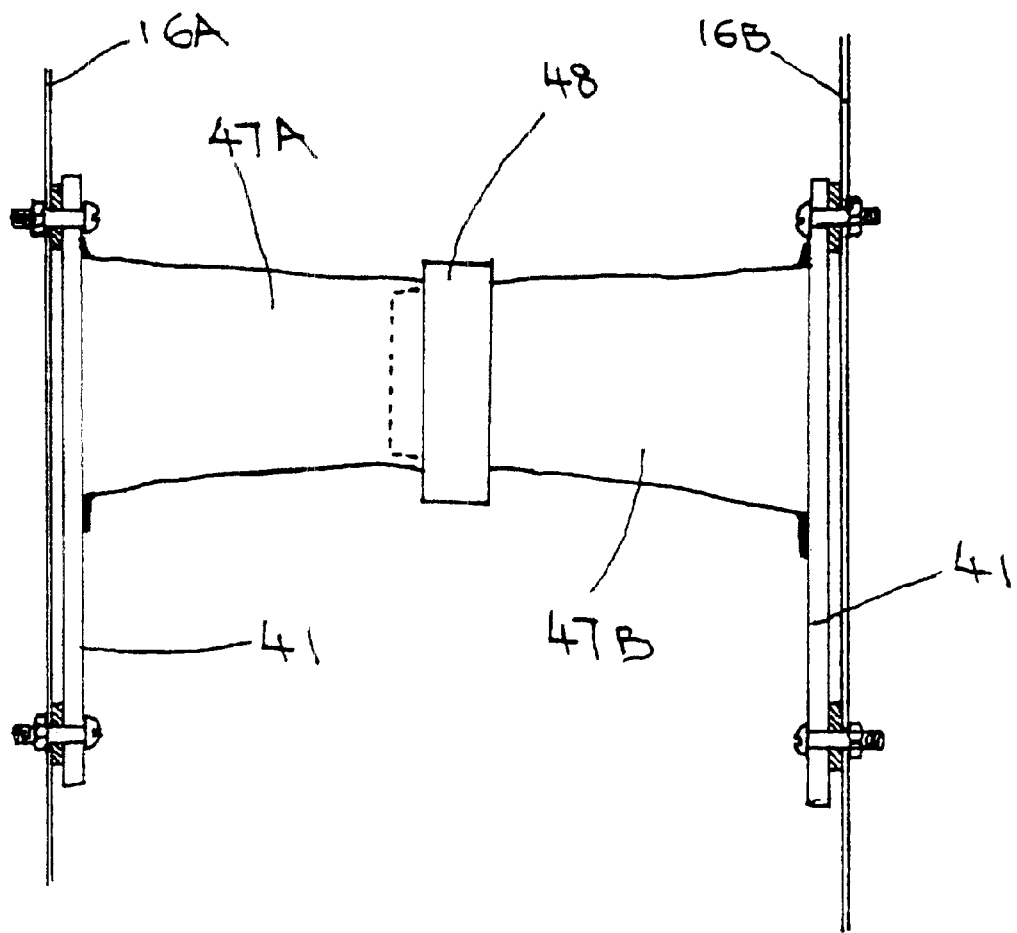
FIG. 12 illustrates a connection between ducts of adjacent containers.
Figure 13:
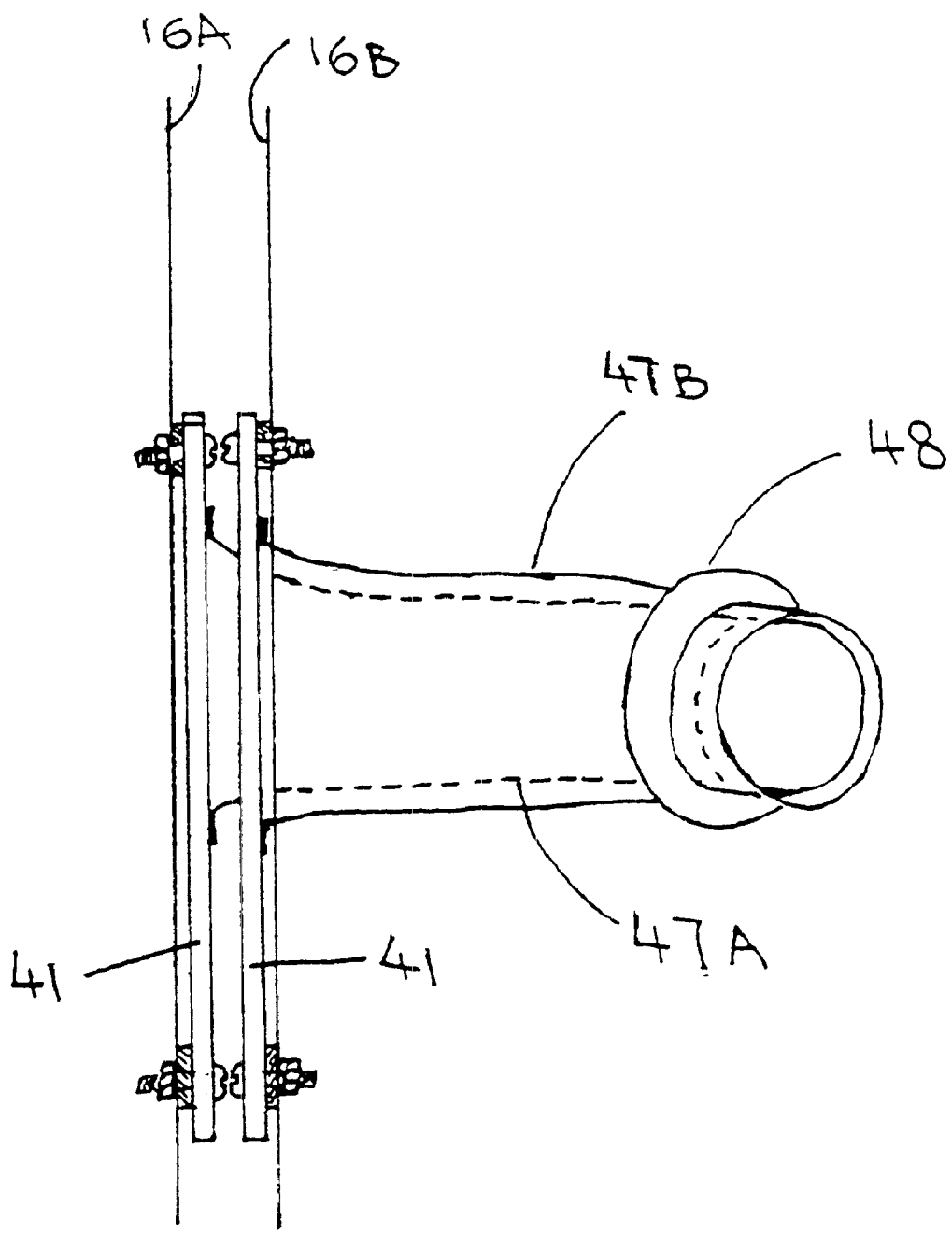
FIG. 13 illustrates another embodiment of an alternate connection between ducts of adjacent containers.

FIG. 12 shows how two flexible ducts 47A, 47B from adjacent containers 16A, 16B are able to be connected by a coupling 48 which comprises a pair of rings, one ring on each of the ducts, such that the ducts are connected when the pair of rings are forced together with a friction fit. Other mechanisms may be contemplated to produce the connection of the ducts, for instance, catches or screw threaded ends may be used. In an alternative embodiment, FIG. 13 shows how two flexible ducts from two adjacent containers 16A, 16B are joined together when the adjacent containers are juxtaposed closely. In this embodiment, the duct 47A from one container 16A is sheathed within the duct 47B of the other container 16B in a male-female connection. The ends of the ducts are held together with a coupling 48.

Interconnections of containers is best effected between containers that are shaped orthogonally, because when orthogonally shaped containers are placed side by side, the flat walls discourage the adjacent containers from rotating. In contrast, when the containers have rounded surfaces, the suspended bags may have a tendency to swivel, and this could place stress on the vents that inter-connect the containers. Thus, in those arrangements that do not have the benefit of upright-walled container, the vents should be designed with sufficient slack, so that they do not become taut in the event that the containers rotate slightly.

The vents are designed to allow liquid to flow through the vents. In the embodiment in FIG. 11, the opening at level A—A is adjusted to the level required in accordance with the density scale, as has been described in connection with FIGS. 8 and 9. However, in the present embodiment of FIG. 11, the opening is surrounded by a flexible duct 47. The flexible duct is able to channel or direct the overflow liquid to another location where it is required to fill other of the containers, rather than letting the liquid overflow out of the full container. The exit of liquid from the container is controlled by the height at which the slit 39 is blocked by the slidable plate 41 of FIG. 11. Therefore, since the flexible vent is controlled to the opening in the plate 41, liquid is able to flow through the flexible duct 47, wherever the plate is slidably located along the grooves 42.

Thus, the vent may either be elongated in shape to encompass the entire slit 39, or may be removably attached at different points on the calibrated density scale device 40 to match the positioning of the opening created by the plate 41.

The function of the vents is to provide an interconnection between apparatus 16 in the arrangement. It is assumed that the vents could connect adjoining containers, but it is conceivable that is the vents are formed in lengths, such as hoses, the vents may connect containers in the arrangement that are not directly adjacent. An example is shown in FIG. 6 in which the upper and lower apparatus 16A, 16B are not directly adjacent.

Procedure For Filling Arrangements of Plurality of Interconnected Apparatus

In the prior art, when a number of bags are used together, it is beneficial to fill the bags simultaneously, otherwise the overall arrangement of bags might become unstable if a few bags on one side of the arrangement gain mass more rapidly that other bags. The problem is that to fill all the bags simultaneously, a number of hoses must be at hand to fill all the bags simultaneously.

In contrast to the prior art, in the present invention, arrangements of a plurality of containers are able to be interconnected. Liquid can flow between the containers. Filling of the containers in the arrangement might start, for example, with filling just one container, preferably one which is close to the center of gravity of the entire arrangement. Subsequently, liquid from this initially-filled apparatus flow to one or more of the other apparatus. Since there are no apparatus in the arrangement that are cut off from the circulation of liquid in the arrangement, the liquid is able to find its own level throughout the arrangement, and eventually fill all the apparatus in the arrangement. This filling of all the containers is achieved by using only a single hose or pump, rather than a number of hoses as was required in the prior art.

For example, in FIG. 5, liquid is first poured into the center container 16A. The adjacent containers 16B on either side of the center container 16A receive liquid that flow from the center container 16A. In FIG. 6, another example is shown where the upper apparatus 16A is filled initially. Once the upper apparatus 16A is filled, liquid exits the upper container and flows down to the lower apparatus 16B suspended beneath. The containers 16A, 16B are interconnected by a lengthy vent in the form of a long hose 37. The end portions of the hose 37 are secured to the respective apparatus by coupling or other suitable water-tight fastening mechanism.

It must be borne in mind that the test mass created by such structures must be accurate often to within ±1% of the specified mass. This is achievable, in the present embodiment, because each one of the apparatus in the overall arrangement is provided with a means for determining the mass of liquid inside the container. In the simplest embodiments, this is achievable by the user ensuring that each container is filled to the correct height necessary to create the specified mass. For example, if the embodiment in FIG. 5 is to be filled with water from a nearby river, the user would start by ascertaining the density of the river water. Next, the liquid density meter 20 on each container is adjusted to indicate the correct level of water required for each container. Then the containers are each filled to the correct level prescribed the liquid density meter 20 on the container. Thus, the total mass of the arrangement—being the combined mass of the individual apparatus—would be accurately determined. In more refined embodiments, each apparatus may be provided with one or more of the sluice valves illustrated in FIG. 8. When water reaches the level determined by the valve, excess water either empties to the ground, or is directed through vents to another of the apparatus. Thus, the level of water in each apparatus in the arrangement is individually controlled by its own "determination means". Since the mass of each individual apparatus is guaranteed to be accurate when filled to the level prescribed by the liquid density meter, the total mass of the overall arrangement is thereby ensured.

Figure 7:
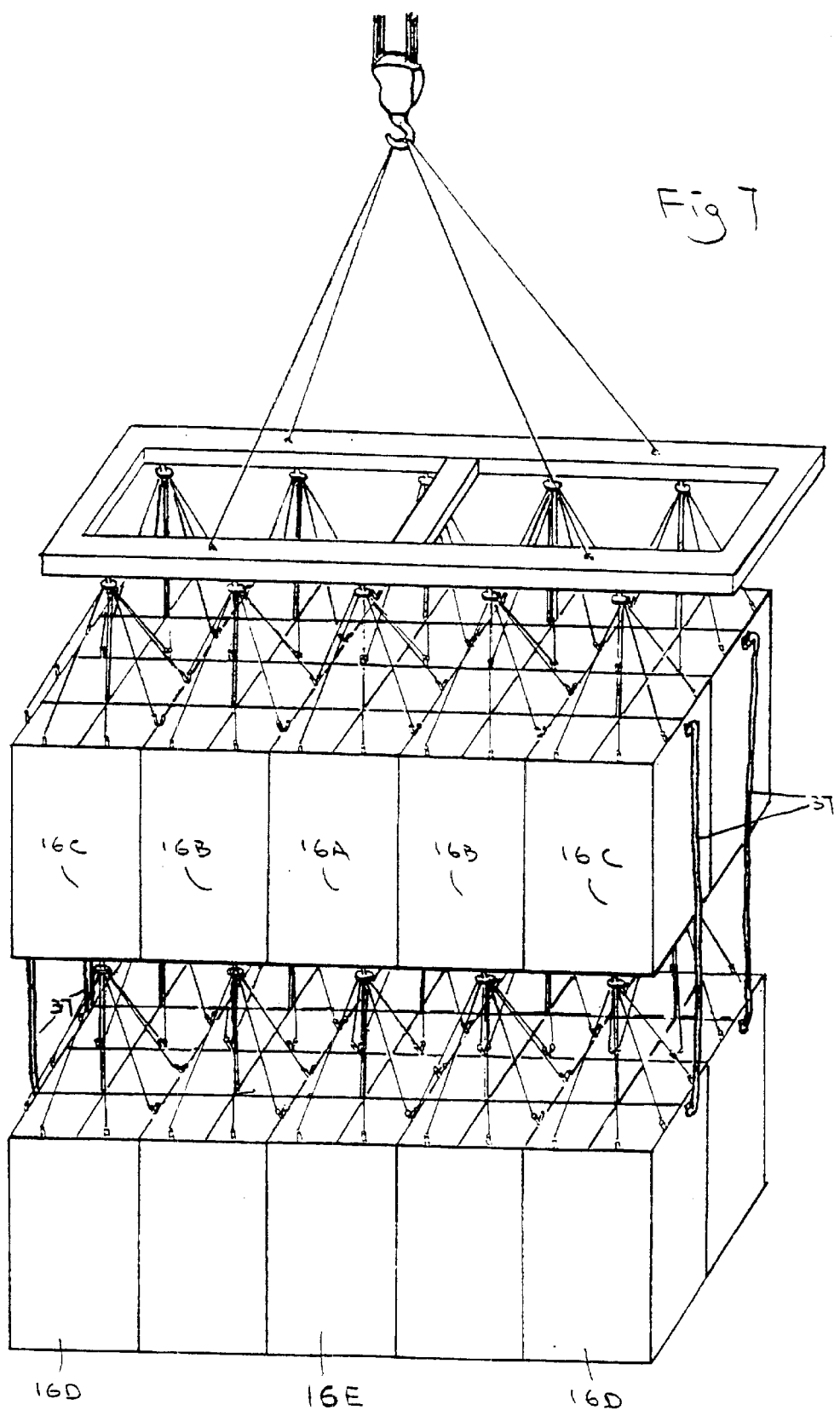
FIG. 7 illustrates a more complex embodiment of the invention consisting of an arrangement of twenty load creation apparatus arranged in two tiers.

FIG. 7 shows a much more complex arrangement of a plurality of apparatus. In these complex and large arrangements, there is a particular benefit of interconnecting the containers, because it ensures that a large arrangement will be filled with liquid without becoming unstable during the filling process. It would be extremely dangerous for such a large mass of liquid, which might be several hundred or thousand tonnes, to suddenly become unstable.

In FIG. 7, one possible procedure would be to commence filling by pouring liquid into the center apparatus 16A of the upper tier. Liquid from these center apparatus 16A would flow equally to the adjoining apparatus 16B, and eventually to the end apparatus 16C. Thus, the top tier of apparatus would be filled while maintaining overall stability of the arrangement. Subsequently, liquid from the end containers would be directed down to the lower tier through vents in the form of elongated hoses 37 found on either side of the overall arrangement. Next, the outer apparatus 16D of the lower tier would begin to fill, and so forth until the overall arrangement of a plurality of apparatus has been filled.

In embodiments that have a plurality of containers, a "determination means" is used which is a modification of the sluice valve of FIGS. 8, 9 and 9A. The modification is shown in FIG. 10. A slideable plate 41 in FIG. 10, which is also slideably mounted in the slot between grooves 42, is different in the sense that the upper end A—A of the plate is guarded by a float valve 45. The float valve 45 pivots about an axis shown as A—A in FIG. 10. The benefit of providing a closeable float valve will be explained as follows, with reference to the filling sequence described for FIG. 7:

The containers in each apparatus are provided with calibrated slits 39 on all four sides of the container walls through which liquid is able to exit the container. The slits 39 on adjacent containers would be connected by a vent. However, those slits 39 that are located on a face of the container that is not adjacent another container would, if left open, act as an opening through which liquid would escape from the overall arrangement, rather than being directed to another container in the arrangement. Therefore, in practice, float valves 45 are used to block all except usually one of the externally-facing slits of the apparatus on the tier. Only one, or at least a very limited number, of the externally facing slits on the same tier are left open without the use of a float valve. Preferably, this one, or limited number of open valves, is located at a point where the liquid will reach at or close to the end of the filling sequence. So, in the example of the filling sequence of FIG. 7, all the containers will be provided with float valves, except for the container 16E on the lower tier, which is exposed to receive liquid only towards the end of the filling sequence. The level of these opened slits are set using the previously described calibrated gauge of FIG. 9A. The location of the open slit or slits (i.e. those not controlled by a float valve) would tend to be as far away from the point at which liquid is poured into the arrangement. This ensures that by the time excess liquid begins to drain through the open slit or slits, the likelihood is that all or most of the containers in the arrangement would have been filled. All the apparatus in the upper tier are filled in the sequence described above.

When liquid in each container reaches the level of the float valve 45, the float shuts off the slits that are located in the externally-facing slits. This would cause each container with a slit blocked by a float valve to temporarily over-fill, so that the excess liquid has to flow out of the container into an adjoining container through the interconnecting vents. Since all the containers in the upper tier are interconnected by vents, any excess liquid in any of the containers can ultimately drain out from the limited number of fully opened valves. Since liquid flows downwards, the one or limited number of valves with open slits should be placed at the lowermost apparatus, or the apparatus in the arrangement or tier to which the liquid is expected to reach last. For example, in the filling sequence of FIG. 7 described above, the container 16E in the middle of the lower tier is provided a valve with an open slit.

In summary, the use of float valves for all except a limited number of the externally facing slits ensures that all the containers in the tier are filled substantially before any liquid is allowed to overflow from the upper tier into the lower tier. As liquid drains out of the limited number of fully opened slits, the liquid level in the over-filled containers begins to fall. When the liquid level drops to the level A—A of the float valve of FIG. 10, the float valve pivots open, and the liquid in each container stops draining out of the container. Thus, every container in the arrangement achieves the right level of liquid necessary for it to create its required mass. This is achieved by using only one liquid source, and obviates the need for having a separate hose for each container.

When a plurality of apparatus are interconnected, filling should commence with the highest container in the arrangement, since water only flows downwards.

In summary, the use of the present embodiment is considered to be very straightforward. To create a test mass, the required number of apparatus are suspended such that the load bearing structure is able to bear the apparatus. The apparatus are interconnected. The density of the liquid is ascertained, and the gauge for each container is set accordingly. Then a hose is used to fill one of the containers, and eventually all the containers will be filled to the correct amount to accurately produce the specified test mass.

When the test for the load bearing apparatus has been completed, the liquid is drained from the apparatus by opening the outlet valve 30. The bag can be folded and stored for further use.

The fact that the present invention is able to create an accurate mass without relying on a weighing device, means that the present invention is able to be used in proximity to flammable materials without the degree of danger that would be associated if an electrical weighing device were to be required.

With the present invention, the need for a weighing device is obtained. However, ironically perhaps, the accurate test masses created by the present invention can actually be used for calibrating such weighing devices.

Compressive Load Testing

Figure 14:
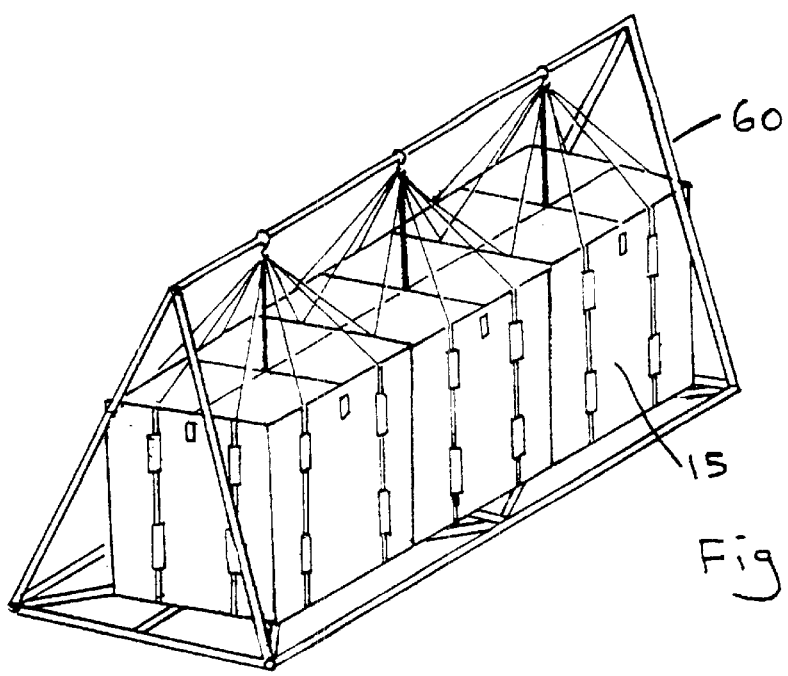
FIG. 14 illustrates an embodiment of a load creating apparatus that is suspended by a rig, such that a structural foundation pile is able to bear the mass created by the load bearing structure.

FIG. 14 illustrates an embodiment of a load creating apparatus that is suspended using a suspensions means, in such a manner that a foundation pile 50 is able to bear the load created by the apparatus. In this embodiment, the suspension means is in the form of a rig 60.

The load creation apparatus 15 is suspended from the test rig 60 which imparts the mass to the foundation pile 50. The containers 16 of the load creation apparatus 15 are suspended from the rig 60, and filled with liquid to create the specified test mass required to test the pile.

Figure 15:
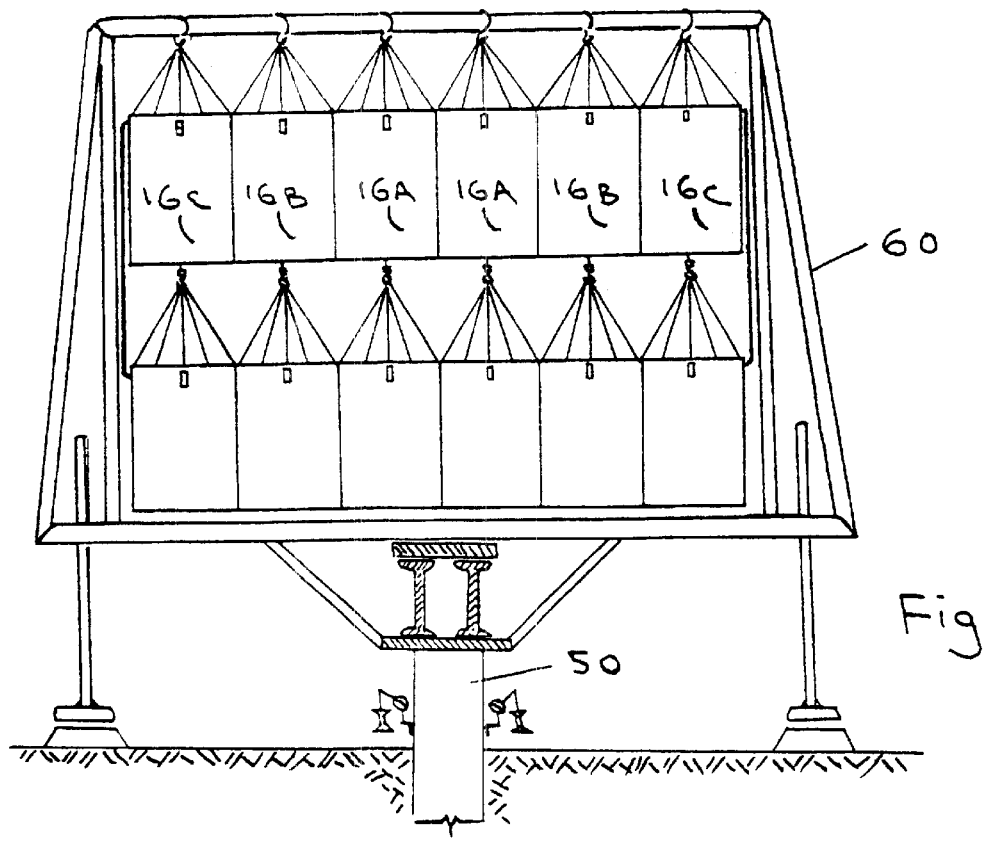
FIG. 15 is a side view of an embodiment similar to that of FIG. 4, except that the embodiment in FIG. 15 uses two decks of containers.

FIG. 15 is a side view of a similar embodiment to that of FIG. 14 which uses two decks of containers.

In some testing procedures, such as A.S.T.M. D 1143, the load must be added in increments of 25%. For instance, the initial load is applied first at 25% of the pile design load. Then the load is increased to 50%, then 75%, then 100% of the design load, each time the load is borne by the structure for several hours to provide time to observe any settling of the pile. Then, the load is decreased in similar increments. Embodiments of the load creation apparatus are ideally suited to adding and taking away precise percentages of the pile design load. The incremental increase and decrease of the load would be more easily accomplished than in the case where the load is created by solid blocks of concrete.

In the embodiment of FIGS. 14 and 15, a compressive load is borne by the load bearing structure. In addition to foundation piles, other load bearing structures that may be tested include bridges, wharf decks, jetties, and other static load bearing structures. Even surfaces such as floors and decks may have a stipulated load bearing capacity, and these structures may also be tested using embodiments of the invention.

The embodiments have been described by way of example only, and modifications are possible within the spirit and scope of the invention as defined by the appended claims. The invention and appended claims, however, do not relate or extend to cover containers, apparatus or methods in general that are not adapted or designed specifically for load creation purposes.

What is claimed is:

1. A load creation apparatus adapted to create a specified mass for testing a load bearing structure, comprising:
    a liquid impervious container having walls;
    reinforcement means for reinforcing the container having first and second pair of sidewalls, each of said first and second pairs of sidewalls having a first sidewall opposing a second sidewall for bracing said first sidewall against said second sidewall in each of said first and second pair of sidewalls, the sidewalls being respectively adjacent the walls of the container;
    the container having means for filling with liquid to create a mass;
    suspension means for suspending the container such that said load bearing structure is able to bear said mass; and
    wherein the container a known volume for determining the mass of any liquid in the container from a density and a volume of the liquid.

2. An apparatus according to claim 1 wherein the container is substantially shaped as a regular geometric shape at least at one region that is adjacent the liquid in the container such that the known volume of liquid in said container is readily calculatable.

3. An apparatus according to claim 1 wherein the container has walls which, in use, are upright at least at one region that is adjacent the liquid in the container.

4. An apparatus according to claim 3 wherein said walls, in use, are generally vertical at the region that is adjacent liquid in the container.

5. An apparatus according to claim 1 wherein the container has a base that has a predetermined surface area.

6. An apparatus according to claim 5 wherein said base is orthogonal.

7. An apparatus according to claim 5 wherein said base is level.

8. An apparatus according to claim 1 wherein said container includes a calibrated gauge which provides a visual indication of a level of liquid to which the container must be filled when the liquid has a particularly density.

9. An apparatus according to claim 8 wherein said visual indication is adjustable in accordance with a density of the liquid.

10. An apparatus according to claim 1 wherein the liquid impervious container is made of flexible material.

11. An apparatus according to claim 1 wherein said means for filling comprises an opening for said container.

12. An apparatus according to claim 1 further including a means for emptying the container comprising a liquid discharge valve in a base of the container.

13. An apparatus according to claim 1 wherein the suspension means comprises a central strap which extends generally through a center of gravity of said container when a liquid is in the container.

14. An apparatus according to claim 1 wherein said container is divided into partitions by an internal web that connect internal surfaces of the container, said web functioning as a structural brace for the container when the container contains liquid.

15. An apparatus according to claim 14 wherein liquid is able to flow from one partition to an adjoining partition through a vent located in the web.

16. An apparatus according to claim 3, wherein the walls of the container are provided with flat reinforcing components which enable the walls, in use, to remain upright.

17. An apparatus according to claim 3 wherein at least one of the walls of the container are connected one to another with reinforcing struts, each of the struts functioning as a structural brace for the container when the container contains liquids.

18. Use of an apparatus according to claim 1 for testing the ability of the load bearing structure to bear a specified test mass.

19. A method of testing the ability of a load bearing structure to bear a specified test mass, comprising the steps of:
    using suspension means to suspend at least one load creation apparatus such that a load bearing structure is able to bear a mass created by said load creation apparatus, said apparatus comprising a liquid impervious container having at least two pairs of opposing walls;
    filling said container with liquid to create said mass;
    bracing said at least two pairs of opposing walls to maintain a substantially constant volume within said container; and
    determining said mass of the liquid from a volume and a density of the liquid.

20. A method according to claim 19 wherein said method involves the step of ascertaining the volume and density of the liquid and thereby determining the mass of the liquid therefrom.

21. A method according to claim 19 wherein said container has walls which, in use, are upright at a region that is adjacent the liquid in the container and said container being provided with a base that has a predetermined surface area, and wherein said method involves the step of calculating the volume of said liquid by multiplying the base surface area by a height of said liquid in the container and determining a value of the mass of the liquid there from.

22. A method according to claim 19 wherein said method involves the step of ascertaining the density of liquid and thereby determining an amount of liquid with which to fill the container in order to produce the specified mass.

23. A method according to claim 19 wherein the method further comprises pouring liquid initially into one of a plurality of apparatus, and wherein liquid from said one apparatus flows to at least one other of said plurality of apparatus.

24. A method according to claim 23 wherein the method further comprises providing each of one or more of said other apparatus with a valve which prevents the liquid from escaping from the apparatus such that the liquid flow to at least an other of said apparatus until all the apparatus in the arrangement have been substantially filled to a required level.

25. A method according to claim 24 wherein said valve is a float valve and wherein the method further comprises opening and closing the float valve by a floatable mechanism.

26. A load creation apparatus adapted to create a specified mass for testing a load bearing structure, comprising:
   a liquid impervious container;
      the container having a means for filling with liquid to create a load; and
   suspension means for suspending the container such that said load bearing structure is able to bear said mass;
   said container having at least two pairs of opposing upright walls, and
   a reinforcing means for reinforcing the walls of the container, the reinforcing means bracing each of said two pairs of opposing upright walls to maintain a substantially constant volume.

27. A load creation apparatus according to claim 26, wherein said walls are generally vertical in a region adjacent a liquid in the container.

28. Use of an apparatus according to claim 1 for testing the ability of the load bearing structure to bear a specified test mass, the load bearing structure being a foundation pile.

29. A load creation apparatus adapted to create a specified mass for testing a load bearing structure selected from the group consisting of a hoist, a crane, a davit and a winch, comprising:
   a liquid impervious container having walls;
   reinforcement means for reinforcing the container having first and second pair of sidewalls, each of said first and second pairs of sidewalls having a first sidewall opposing a second sidewall for bracing said first sidewall against said second sidewall in each of said first and second pair of sidewalls, the sidewalls being respectively adjacent the walls of the container;
   the container having means for filling with liquid to create a mass;
   suspension means for suspending the container such that said load bearing structure is able to bear said mass; and
   wherein the container has a known volume for determining the mass of any liquid in the container from a density and a volume of the liquid.

* * * * *